(12) United States Patent
Al-Ghazzewi et al.

(10) Patent No.: US 8,137,706 B2
(45) Date of Patent: Mar. 20, 2012

(54) PREBIOTIC

(75) Inventors: Farage Al-Ghazzewi, Glasgow (GB); Richard Tester, Glasgow (GB)

(73) Assignee: Glycologic Limited, Glasgow (GB)

( * ) Notice: Subject to any disclaimer, the term of this patent is extended or adjusted under 35 U.S.C. 154(b) by 1002 days.

(21) Appl. No.: 11/596,407

(22) PCT Filed: May 16, 2005

(86) PCT No.: PCT/GB2005/001888
§ 371 (c)(1), (2), (4) Date: Jan. 16, 2008

(87) PCT Pub. No.: WO2005/111195
PCT Pub. Date: Nov. 24, 2005

(65) Prior Publication Data
US 2008/0226603 A1    Sep. 18, 2008

(30) Foreign Application Priority Data
May 14, 2004 (GB) .................................. 0410785.0

(51) Int. Cl.
*A61F 13/00* (2006.01)
*A61K 9/00* (2006.01)
*A61K 36/00* (2006.01)
*A01N 65/00* (2009.01)

(52) U.S. Cl. .................. 424/725; 424/400; 424/433

(58) Field of Classification Search .................. None
See application file for complete search history.

(56) References Cited

U.S. PATENT DOCUMENTS
6,241,983 B1    6/2001    Paul et al.
2002/0051841 A1    5/2002    Chiu et al.

FOREIGN PATENT DOCUMENTS
WO    WO 00/33854    6/2000
WO    WO 04/000340    12/2003
WO    WO 2004/032639    4/2004

OTHER PUBLICATIONS

Jinle et al.: "Development of Research on Konjac Glucomannan Oligosaccharides," *China Food Additives*, pp. 4 (Chinese language), pp. 9 (English Translation), 2004.

Mizutani, T., et al., "Effect of Konjac Mannan on Spontaneous Liver Tumorigenesis and Fecal Flora in C3H/He Male Mice", *Cancer Letters*, (1982), 17:27-32.

Hsiao-Ling, C., et al., "Unhydrolyzed and Hydrolyzed Konjac Glucomannans Modulated Cecal and Fecal Microflora in BALB/C Mice", *Nutrition*, (2005) 21:1059-1064.

*Primary Examiner* — Debbie K Ware
(74) *Attorney, Agent, or Firm* — Janet Sleath; Speckman Law Group PLLC

(57) ABSTRACT

Carbohydrates, in particular mannose containing carbohydrates, are used as a promotor of cell growth. Specifically, polysaccharide hydrolysates are shown to have superior efficacy in promoting the growth of cells, synbiotic foods, prebiotics and pharmaceutical compositions containing mannose containing carbohydrates and polysaccharide hydrolysates described.

23 Claims, 6 Drawing Sheets

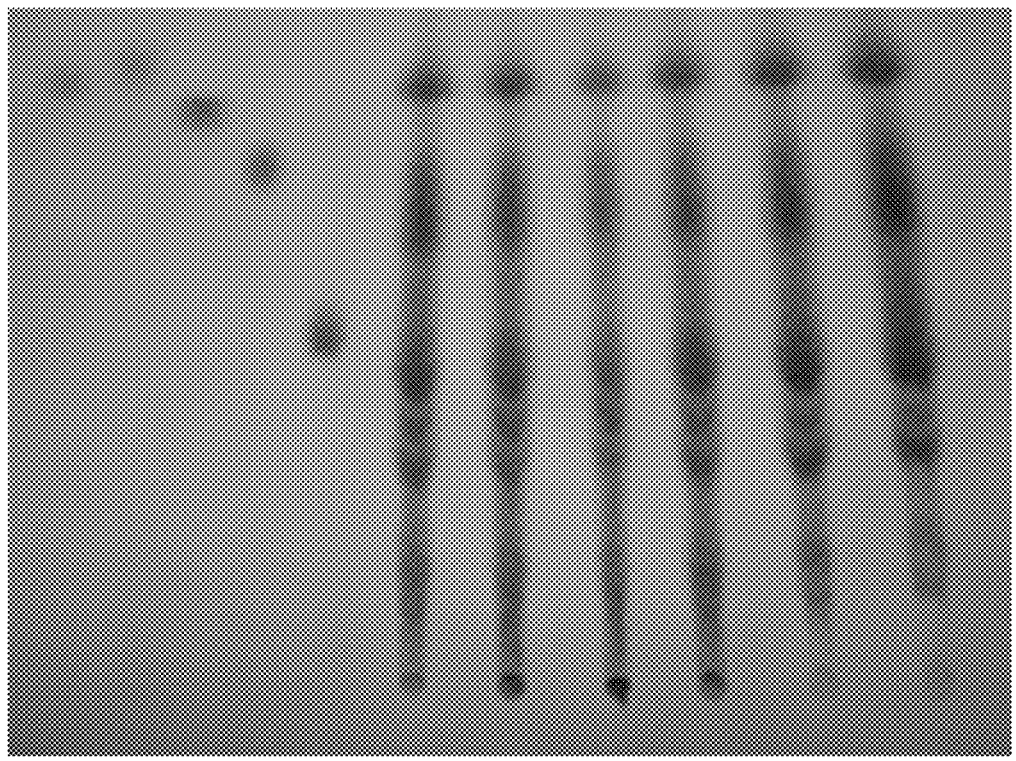
Figure 1 – Chromatograms showing the effect of time, temperature and enzyme concentration. From left to right, the standard sugars glucose, mannose, cellobiose, maltotriose, maltohexaose, 2 hours incubation with 10mg, 15mg, 20mg and 4 hours incubation with 10mg, 15mg, 20mg enzyme/ml respectively.

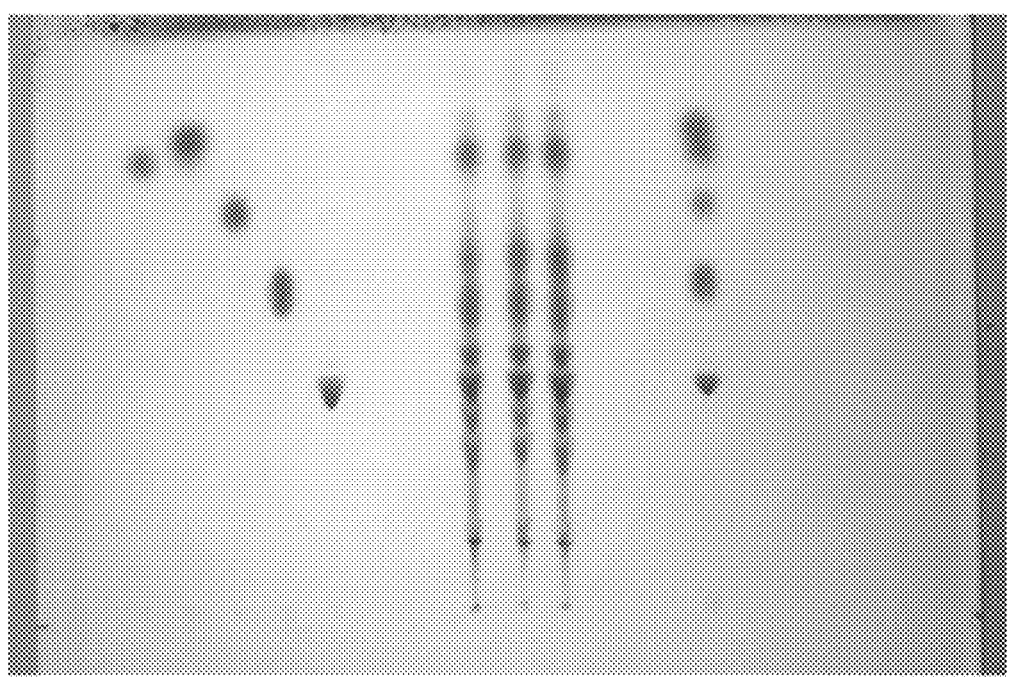
Figure 2 - Chromatograms showing the effect of time and enzyme concentration. From left to right, the standard sugars glucose, mannose, cellobiose, maltotriose, maltohexaose, 4, 3 and 2 hours incubation with 10mg, 15mg and 20mg enzyme/ml buffer respectively at 60°C.

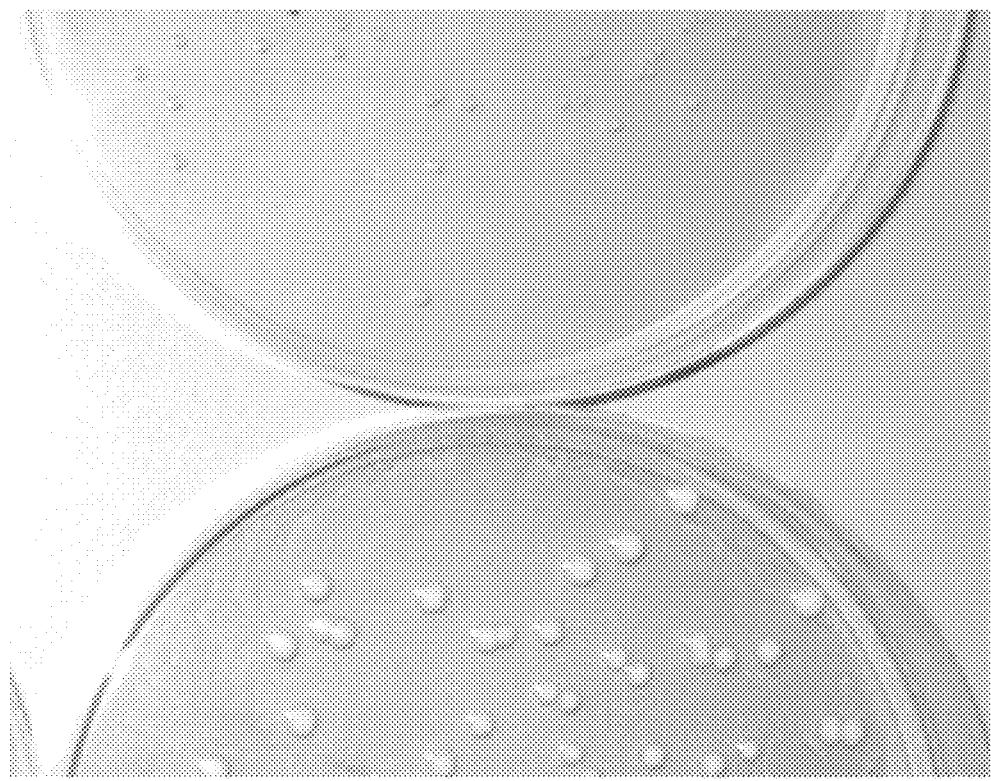
Figure 3. Difference in growth of *Lactobacillus acidophilus* NCFB 1748 on konjac hydrolysate (bottom) and inulin (top).

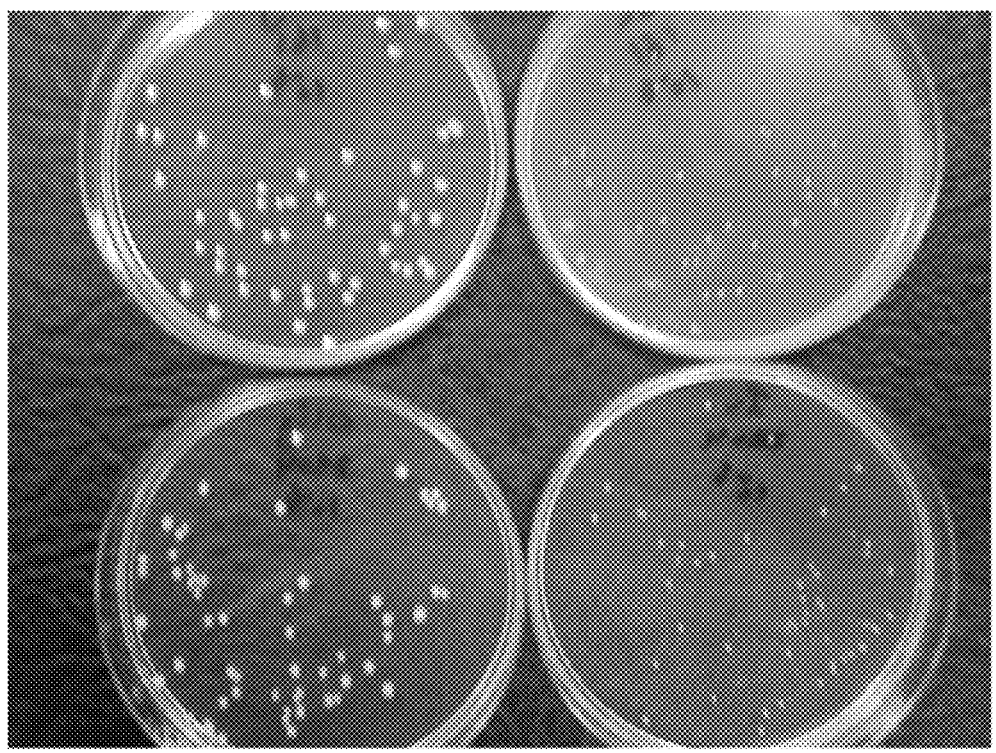
Figure 4. Difference in growth of *Lactobacillus casei* NCFB 161 (top) and *Bifidobacterium adolescentis* NCIMB 702204 (bottom) on konjac hydrolysate (left) and inulin (right).

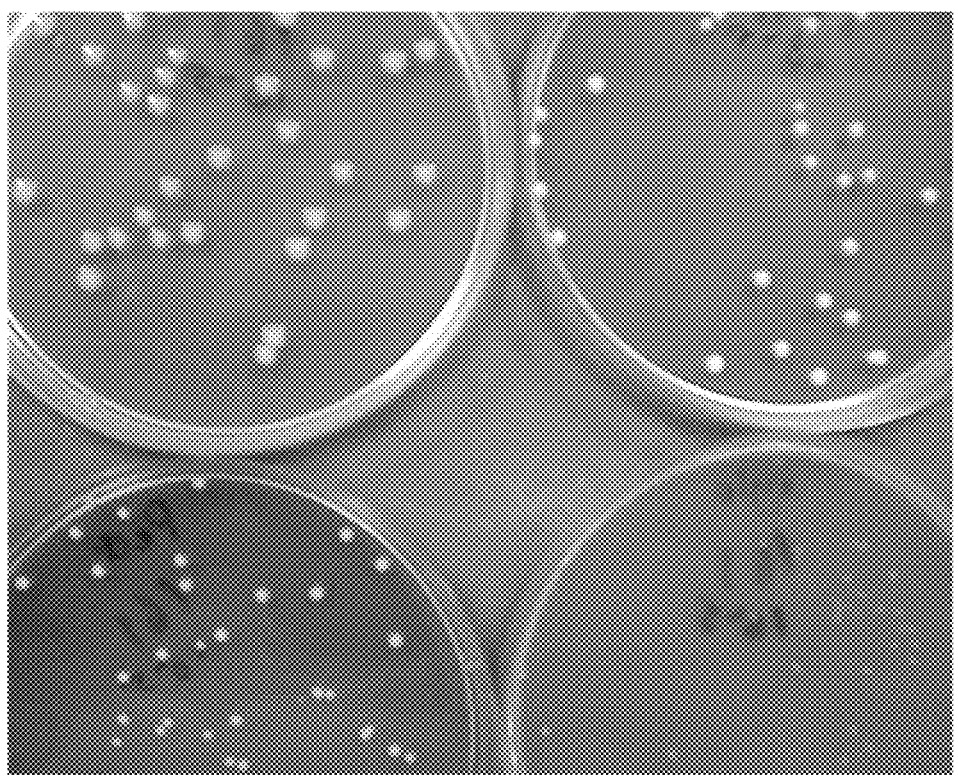
Figure 5. Difference in colony size of *L. casei* NCFB 161 grown (clockwise) on MRS with konjac hydrolysate, MRS agar, MRS with xylohydrolysate and MRS with pectic hydrolysate.

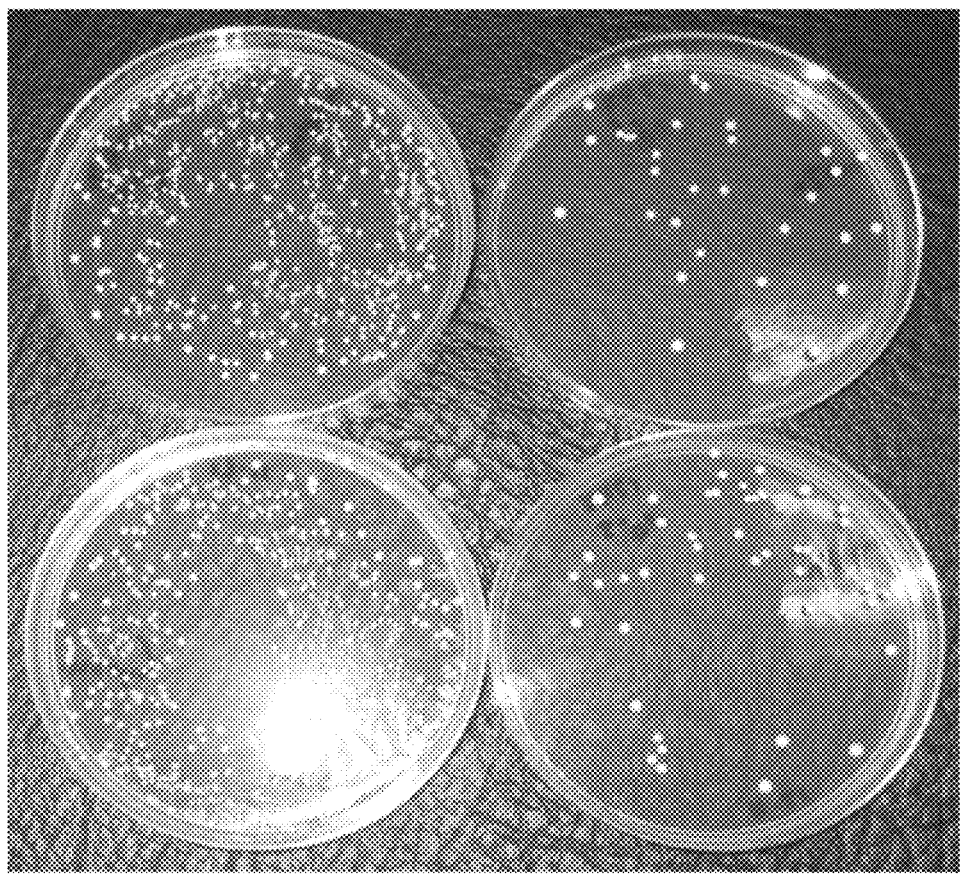
Figure 6. Growth of *Lactobacillus acidophilus* NCFB 1748 on konjac hydrolysate (left) and inulin (right) added to milk, incubated then subcultured on MRS agar.

PREBIOTIC

This application is the US national phase entry of PCT/GB2005/001888, filed May 16, 2005, which claims priority to GB patent application no. 0410785.0, filed May 14, 2004.

FIELD OF THE INVENTION

The present invention relates to prebiotics and in particular to an improved prebiotic for promoting the growth of certain bacteria on nutrient plates, as well as in food and drink, feeds, and in healthcare and pharmaceutical applications.

BACKGROUND

According to Jones (2002) functional foods are defined broadly as 'foods that provide more than simple nutrition; they supply additional physiological benefit to the consumer.' Prebiotics are a specific class of functional foods. According to Jones (2002) they may be defined as 'an indigestible food ingredient that beneficially affects the host by selectively stimulating the growth or activity, or both, of one bacterium or a limited number of bacteria in the colon, thus improving the host's health'. Examples include: neosugars, inulin, soy hydrolysates, isomaltooligosaccharides, galactooligosaccharides, xylooligosaccharides, lactulose, raffinose, sorbitol, xylitol, palatinose and lactosucrose.

Prebiotic bacteria have a positive and beneficial effect in the gut of man. Examples are *Lactobacilli* spp and *Bifidobacteria* spp. More details may be found in recent reviews (Loo et al, 1999; Topping and Clifton, 2001; Tomasik and Tomasik, 2003). Both pre- and probiotic foods may be consumed together to promote the colonisation of probiotic bacteria in the gut.

Glucomannans are neutral polysaccharides produced by many plants where they serve as energy reserves and in some cases structural roles. The polysaccharides comprise, in most cases, predominantly mannose residues with glucose as the second sugar. The polysaccharides contain some acetylated residues and may contain some galactose side chains (Khanna, 2003). Sources of glucomannans are presented in Table 1.

TABLE 1

Glucomannans from different sources

| Source | Mannose:Glucose Ratio (MGR) | Degree of Polymerisation (DP) |
| --- | --- | --- |
| Eastern white pine (*Pinus strobes*) | 3.8:1 | 90 |
| Higanbana (*Lycoris radiata*) | 4.0:1 | 730 |
| Konjac (*Amorphophallus konjac*) | 1.6:1 | >6,000 |
| Lily (*Lilium auratum*) | 2.7:1 | 220 |
| Orchid (*Tubera salep*) | 3.2:1 | 600 |
| Ramie (*Boehmeria nivea*) | 1.8:1 | nd |
| Redwood (*Sequois sempervirens*) | 4.2:1 | 60 |
| Suisen (*Narcissus tazetta*) | 1.5:1 | nd | nd: not determined
Adapted from Khanna (2003)

From Table 1, it is evident that glucomannans can be extracted from a broad range of different botanical sources where there is variability in molecular weight and mannose to glucose ratio.

Konjac glucomannan is a polysaccharide extracted from the *Amorphophallus konjac* plant (or group of plants) which is, itself, a member of the *Araceae* genus. Konjac corms have been grown as food for centuries in Asia where they have provided a source of food with very interesting physical characteristics (Thomas, 1997; Khanna, 2003). The flour produced from konjac corns is used as a gelling and thickening agent and is a permitted food ingredient (Europe, E425). The principal polysaccharide component of konjac corn is a glucomannan that has exceptionally high swelling characteristics when hydrated. The flour has been used in gums throughout the world but use for this purpose was recently banned (e.g. Europe) because of the death of eighteen people as a consequence of choking. Other nutritional benefits of the flour include cholesterol lowering, bulking for weight reduction and to reduce the risk of constipation (Khanna, 2003). Apart from food uses, the flour may be used as a film forming material, pharmaceutical excipient, within body care products and as a chromatographic media (Khanna, 2003).

Commercial applications of konjac flour require different purity of the flour with the highest glucomannan content reflecting the highest cost. Purification is usually achieved with sieving procedures and alcohol washing rather than treatment with enzymes (amylases, proteases and lipases to remove non-glucomannan components) per se (Khanna, 2003).

Konjac glucomannans are high molecular weight polymers where the molecular weight typically exceeds $1\times10^6$ D (Khanna, 2003). The sugars are arranged in blocks of mannose and glucose residues that are $\beta$-(1-4) linked with typically 1.6:1 mannose to glucose residues within the polysaccharides. This linear structure is interspersed with branches on C3 of the sugar residues at approximately every tenth hexose unit with an esterified acetyl group at approximately every nineteenth residue (Khanna, 2003).

In the human body, some polysaccharides are defined as for example 'starchy', 'digestible' or 'available' whilst others are defined as for example 'indigestible', 'non-digestible', 'dietary fibre' or 'non-starchy'. The starchy polysaccharides are digestible by mans' digestive enzymes in the small intestine if they are amorphous. If starchy polymers are crystalline they may be carried to the large intestine where they are fermented and are described as 'resistant starch'. Non-starch polysaccharides cannot be digested in mans' small intestine and are always carried to the large intestine where they are fermented. Non-starch polysaccharides and resistant starch together form dietary fibre. This is an apparently important component of the diet as it promotes gut transit of food, provides bulk and satiety and provides a fermentation matrix in the colon. This fermentation releases short chain fatty acids which may be absorbed into the blood stream which is reported to have beneficial effects against gut cancer. Glucomannan polysaccharides would be fermented in the large intestine of man accordingly. For more details regarding the fermentation of polysaccharides in the gut readers are referred to a recent review by Topping and Clifton (2001).

In the present Application the term hydrolysate means material of lower molecular weight than the parent polysaccharide, and includes, but is not limited exclusively to, oligosaccharides and sugars.

The production of hydrolysates from polysaccharides can be achieved by, for example, acid or enzymatic hydrolysis. With respect to mannans (including glucomannans and especially konjac glucomannans) this may be achieved under appropriate conditions too. Acid hydrolysis tends to be random whilst enzymatic hydrolysis is more focused towards specific bonds. Konjac (and non-konjac) glucomannan may be hydrolysed by acids, mannanases and cellulases (Kato and Matsuda, 1969; Kato et al, 1970; Shimahara, 1975; Chiu et al, 1991; Ohya et al., 1994; Behr, 1998; Chiu et al, 1998; Edashige and Ishii, 1998; Kurakake and Komaki, 2001; Cescutti et al, 2002; Chiu et al, 2002; Qi et al, 2003). Hence, the use of cellulases and other enzymes for the purpose of konjac glucomannan hydrolysis has been well established before 1980. It is, perhaps, unusual that the patent described by Chiu et al (1991, 2002) was granted. This concerns the use of cellulases to hydrolyse konjac glucomannans and their use as potential non-digestible bulking agents in foods.

Water soluble konjac (dialysis) extracts have been investigated and published by Shimizu Manzo Shoten KK company (1974) and Sugiyama and Shimahara (1976). Gel systems based on konjac and starch combination have been discussed by Tye et al (1990, 1994). Chiu et al (1991, 1998, 2002) have discussed the use of cellulases to convert konjac glucomannans to oligosaccharides and their use as sugar replacements/bulking agents. King et al (1994) and Wheatley et al (1996) have used konjac glucomannan as a sustained release excipient. Healthcare drinks/compositions containing konjac with or without the addition of other health promoting components have been described (Zhou, 1995; Vuksan, 2001; Sun, 2003).

SUMMARY

There is described herein developments which show that use of mannose containing carbohydrates and in particular mannans such as glucomannans and galactomannans are superior promoters and stimulators of cell and micro-organism growth. Specifically polysaccharide hydrolysates and in particular mannan hydrolysates have been found, in the present invention, to have unexpectedly superior efficacy in promoting the growth of cells. Glucomannans hydrolysates (especially but not exclusively konjac glucomannans) are particularly effective. As a result, a more commercially viable method of preparing supporting organisms in culture (e.g. agar plates), in functional and fermented foods (e.g. yoghurts, cheese and salami) and in healthcare/pharmaceutical products has been developed and is described herein.

According to a first aspect of the present invention there is provided the use of mannose containing carbohydrates to promote the growth of cells.

Preferably the mannose containing carbohydrates are polysaccharides or lower molecular weight materials found in nature.

Most preferably the mannose containing carbohydrates are polysaccharide hydrolysates, derivatives or mannose containing materials with a lower molecular weight than that of polysaccharides found in nature.

Optionally the polysaccharide hydrolysates are enzymatic hydrolysates.

Optionally the polysaccharide hydrolysates are chemical or physical hydrolysates.

Preferably the polysaccharide hydrolysates are mannans. Optionally the mannans are glucomannans. Alternatively the mannans are galactomannans. Alternatively the mannans are other types of mannans.

The mannans may be natural or synthetic.

The mannan may be in the form of mannose syrup, powder or flour.

The glucomannan is optionally konjac glucomannan.

Optionally other carbohydrates may also be added to the cells.

The cells are optionally micro-organisms.

The cells may be bacteria such as *Lactobacilli* spp and *Bifidobacteria* spp.

Alternatively the cells may be other bacteria, yeasts, moulds or fungi.

The mannose containing carbohydrates may be used as a carbon source within animal and human foodstuffs to promote the growth of cells within the product or post ingestion.

The cells are typically micro-organisms.

The cells may be bacteria such as *Lactobacilli* spp and *Bifidobacteria* spp. Alternatively the cells may be yeasts, moulds or fungi.

The animal and human foodstuffs may be nutritional or pharmaceutical food or drinks, feeds or products.

The foodstuff may be a fermenting or fermented product such as yoghurt. The foodstuff may be a functional food.

The mannose containing carbohydrates promote the growth of cells within the intestine and body cavities.

Typically the mannose containing carbohydrates promote the growth of gut friendly cells at the expense of pathogenic organisms.

According to a second aspect of the present invention there is provided a synbiotic food or feed comprising one or more probiotic bacteria and mannose containing carbohydrates.

The synbiotic food or feed may be a prebiotic.

The synbiotic food or feed may be a probiotic.

The symbiotic food or feed may be a mixture of prebiotic and probiotic.

Preferably the mannose containing carbohydrates (mannans) are polysaccharides or lower molecular weight materials (and their derivatives) found in nature.

Most preferably the carbohydrates are polysaccharide hydrolysates (including derivatives) or mannose containing materials with a lower molecular weight than that of polysaccharides found in nature.

Optionally the polysaccharide hydrolysates are enzymatic hydrolysates.

Optionally the polysaccharide hydrolysates are chemical or physical hydrolysates.

Preferably the polysaccharide hydrolysates are mannans. Optionally the mannans are glucomannans. Alternatively the mannans are galactomannans or other types of mannans.

The mannans may be natural or synthetic.

The mannan may be in the form of mannose syrup, powder, or flour.

The glucomannan is optionally konjac glucomannan.

Any suitable probiotic bacteria may be used. Examples include *Lactobacilli* spp and *Bifidobacteria* spp.

The third aspect of the present invention provides for the use of mannose containing carbohydrates as a carbon source for promoting the growth of micro-organisms in man and animals.

The carbon source may promote growth in the gut of man and animals.

The fourth aspect of the present invention provides for the use of mannose containing carbohydrates as a prebiotic for promoting the growth of micro-organisms in man and animals.

The probiotic may promote growth in the gut of man and animals.

Preferably the mannose containing carbohydrates are polysaccharides or lower molecular weight materials found in nature.

Most preferably the carbohydrates are polysaccharide hydrolysates, derivatives or mannose containing materials with a lower molecular weight than that of polysaccharides found in nature.

Optionally the polysaccharide hydrolysates are enzymatic hydrolysates.

Optionally the polysaccharide hydrolysates are chemical or physical hydrolysates.

Preferably the polysaccharide hydrolysates are mannans.

Optionally the mannans are glucomannans. Alternatively the mannans are galactomannans or other types of mannans.

The mannans may be natural or synthetic.

The mannan may be in the form of mannose syrup, powder, or flour.

The glucomannan is optionally konjac glucomannan.

According to a fifth aspect of the present invention there is provided a carbon source for promoting the growth of micro-organisms in man and animals; the prebiotic comprising mannose containing polysaccharide hydrolysates or synthetic derivatives with a lower molecular weight than mannan containing polysaccharides found in nature.

The carbon source may promote growth in the gut of man and animals.

According to a sixth aspect of the present invention there is provided a prebiotic for promoting the growth of micro-organisms in man and animals; the prebiotic comprising mannose containing polysaccharide hydrolysates or synthetic derivatives with a lower molecular weight than mannan containing polysaccharides found in nature.

The carbon source may promote growth in the gut of man and animals.

Preferably the mannose containing carbohydrates are derived from polysaccharides but may be lower molecular weight materials than found in nature.

Most preferably the carbohydrates are polysaccharide hydrolysates, derivatives or mannose containing materials with a lower molecular weight than that of polysaccharides found in nature.

Optionally the polysaccharide hydrolysates are enzymatic hydrolysates.

Optionally the polysaccharide hydrolysates are chemical or physical hydrolysates.

Preferably the polysaccharide hydrolysates are mannans.

Optionally the mannans are glucomannans. Alternatively the mannans are galactomannans or any other types of mannans.

The mannans may be natural or synthetic.

The mannan may be in the form of mannose syrup, powder, or flour.

The glucomannan is preferably (but not exclusively) konjac glucomannan.

The prebiotic or hydrolysate may be suitable for topical, oral, intravaginal or anal administration.

Optionally, the prebiotic or hydrolysate is a pessary in any physical forms such as tablet, capsule, or liquid such as a douche].

Alternatively the hydrolysate or prebiotic is a cream (consumer and healthcare products).

Alternatively the hydrolysate or prebiotic is a suppository (consumer and healthcare products).

The micro-organisms are typically natural microflora.

According to a seventh aspect of the present invention there is provided a pharmaceutical composition, the composition may comprise one or more probiotic bacteria and carbohydrates.

The carbohydrates are preferably mannose containing carbohydrates.

Preferably the mannose containing carbohydrates are polysaccharides or lower molecular weight materials found in nature.

Most preferably the carbohydrates are polysaccharide hydrolysates, derivatives or mannose containing materials with a lower molecular weight than that of polysaccharides found in nature.

Optionally the polysaccharide hydrolysates are enzymatic hydrolysates.

Optionally the polysaccharide hydrolysates are chemical or physical hydrolysates.

Preferably the polysaccharide hydrolysates are mannans.

Optionally the mannans are glucomannans. Alternatively the mannans are galactomannans or other types of mannans.

The mannans may be natural or synthetic.

The mannan may be in the form of mannose syrup, powder or flour.

The glucomannan is optionally konjac glucomannan.

The pharmaceutical composition may be a pessary, suppository or cream or any healthcare products.

BRIEF DESCRIPTION OF THE DRAWINGS

The present invention will now be described with reference to the following Figures in which:

FIGS. 1 and 2 show the effect of time, temperature and enzyme concentration on cellulase hydrolysis of konjac flour;

FIG. 3 shows the results of a comparison in the growth of lactic acid bacteria in media containing konjac hydrolysate (bottom) and in media containing inulin (top);

FIG. 4 shows the results of a comparison in the growth of lactobacilli (top) and bifidobacteria (bottom) in media containing konjac hydrolysate (left) and in media containing inulin (right); and FIG. 5 shows the results of a comparison in the growth of lactic acid bacteria in media containing konjac hydrolysate (top left), media containing MRS Agar (top right); media containing MRS and xylohydrolysate (bottom right) and media containing MRS and pectic hydrolysate (bottom left).

FIG. 6 shows the results of a comparison in the growth of lactic acid bacteria in milk incubated with konjac hydrolysate (left) and milk incubated with inulin (right).

DETAILED DESCRIPTION

Through the experiments discussed in depth below, mannose containing carbohydrates, and in particular, mannans such as glucomannans and galactomannans have been found to be superior promoters of the growth of bacteria. In particular the Applicant has shown that polysaccharide hydrolysates including hydrolysates of konjac glucomannans and galactomannans are excellent promoters of cells and micro-organism growth and have an unexpectedly superior efficacy in promoting this growth when compared to existing commercially well know prebiotic substances. In particular glucomannan hydrolysates promote the growth of gut friendly bacteria like *Lactobacilli* spp and *Bifidobacteria* spp and may be used in animal and human foodstuffs and feeds. Carbohydrates, including mannose containing carbohydrates, have also been found to be excellent prebiotics and promoters of cell and micro-organism growth when given through non-oral administration, for example, by vaginal, topical or anal administration. Carbohydrates such as the mannose containing glucomannan, galactomannan and indeed other types of mannan are hereby envisaged to have use in consumer and healthcare products, such as topical creams, suppositories, douches and pessarys.

The Applicant envisages that mannans and especially mannan hydrolysates such as glucomannan and galactomannan hydrolysates have the potential to:

Promote cell (especially but not exclusively bacterial) growth on nutrient plates. It may also, in this context, provide cryoprotectant advantage during drying of these cells.

Function as an adjuvent in feed, food and drink and healthcare systems where the material can provide a carbon source for organisms within the non-fermenting/fermenting/fermented food.

Function as an adjuvent in feed, food and drink and healthcare systems where the material can provide a carbon source for organisms carried to and located within gut.

Selectively support the growth of certain microorganisms over others in feed, drink, food, healthcare, pharmaceutical, biological and other relevant products.

A key aspect to the commercial advantages provided by this invention lies in the fact that the polysaccharide hydrolysates may be produced by any suitable means, such as chemical (acid), biochemical, enzyme or physical hydrolysates, and are effective regardless of molecular weight or distribution.

The mannan may be pure mannan or in combination with another substance (e.g. sugars). Synthetic mannan may also be used.

Method 1 Cellulase Hydrolysis of Konjac Flour

In order to determine the extent of cellulase 13P-CO13P (Biocatalysts Ltd. Wales, UK) hydrolysis of konjac flour (Luxara 5867, Arthur Branwell & Co. Ltd.), experiments were conducted using different enzyme concentrations. Konjac flour was dissolved in acetate buffer (200 mM, pH 4.5) in 250 ml Duran glass screw neck flasks with different cellulase concentrations. Samples were incubated in a water bath shaker at 60° C. for 2 or 4 hours. A control without konjac with cellulase was also included. Aliquots (1 ml) were transferred by pipette to clean screw top 10 ml tubes, sealed, and then placed in a boiling water bath for 15 minutes in order to inactivate the enzyme. Next, they were centrifuged for 15 minutes at 3000 rpm (1500×g). Aliquots (1 ml) of the supernatants were transferred into 250 ml volumetric flasks by pipette. About 100 ml deionised water was added to the flasks with ml zinc sulphate and 6 ml of 1M sodium hydroxide before they made up to volume with deionised water. The contents were filtered through Whatman No. 1 filter paper (18.5 cm diameter) into 250 ml conical flasks. Aliquots (1 ml) of the clear filtrate for each flask was then transferred into 10 ml screw cap Pyrex tube by pipette for the determination of reducing power (Nelson, 1944).

The supernatant fraction (~0.25 ml) was also separated by Thin-Layer Chromatography (TLC) against standard sugars and hydrolysates in order to give an indication of the chain lengths. Standard sugars used for TLC (Whatman K S silica gel 150° A, Thickness 250 um) were glucose (ACROS Organics-410955000), mannose (Sigma-M-4625), cellobiose (Fluka-22150), multotriose (ACROS Organics-225940010), and multohexaose (Sigma-M9153). The mobile phase used for the TLC plates was comprised of propan-2-ol, acetone and 1M lactic acid (4:4:2 respectively). The different sugars were visualised using diphenylamine (aniline, diphenylamine and 85% orthophosphoric acid with the proportion of 5:5:1 respectively).

The results of this method are shown in FIG. 1. Enzymatic hydrolysis increased by increasing enzyme concentration, temperature and time. As the enzyme concentration, temperature or time was increased, the proportion of low molecular weight material increased as expected. For optimal yields of hydrolysates, the following condition was optimised and chosen for much of the work (although not exclusively): 15 mg cellulase/ml buffer hydrolysed at 60° C. for 2 hours with a solid to buffer ratio of 1:10 as shown in FIG. 2.

Method 2—Extract of Konjac Hydrolysates

Konjac hydrolysates were extracted at the desired conditions in two different ways: (a) without sugars where the supernatant was precipitated by 90% absolute ethanol or (b) with sugars where the supernatant was freeze-dried. The two konjac hydrolysates preparation fractions were compared in terms of functionality (specifically substrates for microorganism growth). This was achieved as follows.

Several lactic acid bacteria were obtained from various sources. These included:

| | |
|---|---|
| *Lactobacillus casei* ssp *casei* | NCFB 161 |
| *Lactobacillus delbruckii* ssp *bulgaricus* | NCFB 1489 |
| *Lactobacillus acidophilus* | NCFB 1748 |
| *Lactobacillus gasseri* | NCFB 2233 |
| *Lactobacillus plantarum* | DSM 12028 |
| *Lactococcus lactis* ssp *lactis* | NCIMB 6681 |
| *Bifidobacterium adolescentis* | NCIMB 702204 |
| *Bifidobacterium breve* | NCIMB 702258 |
| *Bifidobacterium bifidum* | NCIMB 700795 |

The growth of these strains of bacteria was examined using the two konjac hydrolysate preparation fractions. This was conducted by using a Bactometer (bioMerieux, Basingstoke, Hampshire) where a serial dilution was prepared in sterile deionised water for each organism, where 1 ml modified MRS broth was transferred into each well of the disposable Bactometer modules. Each well in the Bactometer module was inoculated with 0.1 ml aliquots of each dilution and then covered with sterile mineral oil for obtaining anaerobic conditions. The modules were then incubated at 37° C. for 48 hours in a Bactometer 128 Microbial Monitoring System (bioMerieux, Basingstoke, Hampshire) driven by Tektronix 4205 software (bioMerieux, Basingstoke, Hampshire). The growth of lactic acid bacteria was also examined by growing the strains in modified MRS agar plates.

The results showed that all strains of lactic acid bacteria used were able to grow with both konjac hydrolysate preparation fractions. In the Bactometer the growth was demonstrated by the detection time (time required for an initial concentration of microorganisms to reach the Bactometer threshold level) shown in the Bactometer modules. It was also shown that there was no significant difference between the two hydrolysate fractions, therefore, it was decided for economical reasons to use the konjac hydrolysate containing sugars in this application—although applications may be made with or without the sugars.

EXAMPLE 1

Use of Glucomannan/Konjac Hydrolysates to Support Bacterial Growth on Media

Konjac Hydrolysate in the Bactometer:

The konjac hydrolysates produced were used as a carbon source to provide the growth of a range of lactic acid bacteria in the Bactometer. De Man, Rogosa and Sharpe (MRS) broth was prepared according to the original recipe and MRS modified broth was prepared by substituting the glucose in the original recipe (20 mg/ml glucose) with 100% mannose to glucose (1.6:1), 100% soluble hydrolysate containing sugars and 100% soluble hydrolysate without sugars. Serial dilutions were prepared in sterile deionised water for each organism. For incubation of organisms and determination of growth rate in the microbial monitoring system, 1 ml broth was transferred into each well of the disposable Bactometer modules (bioMerieux, Basingstoke, Hampshire). Each well in the module was inoculated with 0.1 ml aliquots of each dilution and then covered with sterile mineral oil for obtaining anaerobic conditions. The modules were then incubated at 37° C. for 48 hours in a Bactometer 128 Microbial Monitoring System (bioMerieux, Basingstoke, Hampshire) driven by Tektronix 4205 software (bioMerieux, Basingstoke, Hampshire).

The results showed that all lactic acid bacteria examined including lactobacilli and bifidobacteria grew on all the carbon sources used. This was demonstrated by the detection time (time required for an initial concentration of microorganisms to reach the Bactometer threshold level) shown in the Bactometer modules.

EXAMPLE 2

Konjac Hydrolysate and Inulin in MRS Agar

A comparison in the growth of lactic acid bacteria was made between media containing konjac hydrolysate and another containing inulin, an established prebiotic. In this case, the carbon source was mixed in the MRS media substituting the glucose in the original recipe (20 mg/ml glucose). MRS media with no carbon source, with konjac hydrolysate and with inulin were prepared. A serial dilution with maximum recovery diluents was made and 0.1 ml aliquot of each dilution of each organism was plated using spread plate technique. Plates were then incubated under 5% $CO_2$ conditions at 37° C. for 48 hours after which time colony forming units (C.F.U.) were obtained.

The number of colonies was in the same range ($10^7$-$10^8$) with both carbon sources. However, very big colonies (5 mm) were grown on MRS plates containing konjac hydrolysate. On the other hand, very small colonies (0.5-1 mm) were obtained on MRS plates containing inulin as a carbon source. Results are shown in FIGS. 3 and 4.

EXAMPLE 3

Konjac Hydrolysate and Inulo-Hydrolysate in MRS Agar

Growth of lactic acid bacteria was compared on media containing konjac hydrolysate and another containing inulo-hydrolysate. The konjac flour and inulin were hydrolysed using the appropriate concentration of cellulase and inulinase respectively. The konjac hydrolysate and inulo-hydrolysate produced were added to the MRS agar substituting the glucose in the original recipe (20 mg/ml glucose). A serial dilution with the maximum recovery diluents was made and lactic acid bacteria including 3 lactobacilli and 3 bifidobacteria were subcultured and incubated under 5% $CO_2$ conditions at 37° C. for 48 hours.

TABLE 2

Colony forming units and colony size of Lactic acid bacteria on media containing konjac hydrolysate (KOS) and inulo-hydrolysate (IOS).

| Probiotic strain | IOS | KOS | Colony size (mm) IOS | KOS |
| --- | --- | --- | --- | --- |
| L. casei NCFB 161 | $3.9 \times 10^8$ | $2.5 \times 10^8$ | 1 | 5 |
| L. delbruckii NCFB 1489 | $3.0 \times 10^8$ | $2.4 \times 10^8$ | 1 | 5 |
| L. acidophilus NCFB 1748 | $4.4 \times 10^8$ | $3.2 \times 10^8$ | 1 | 5 |
| B. adolescentis NCIMB 702204 | $2.9 \times 10^8$ | $4.2 \times 10^8$ | 1 | 5 |
| B. breve NCIMB 702258 | $3.0 \times 10^8$ | $3.5 \times 10^8$ | 1 | 5 |
| B. bifidum NCIMB 700795 | $8.7 \times 10^7$ | $8.2 \times 10^7$ | 1 | 5 |

The C.F.U. as shown in Table 2 with both carbon sources were in the range of 2.4–4.4×$10^8$ with the exception of B. bifidum NCIMB (700795) which showed 8×$10^7$. However, the size of colonies on media containing konjac hydrolysate was much bigger (5 mm) than those grown on media containing inulo-hydrolysate (1 mm). This suggests that konjac hydrolysate was supporting the growth of lactic acid bacteria and therefore the generation time was faster than those grown on media containing inulo-hydrolysate.

EXAMPLE 4

Konjac Hydrolysate with Pectic Hydrolysate and Xylohydrolysate in MRS Agar

Growth of lactic acid bacteria was also compared on media containing konjac hydrolysate and others containing pectic hydrolysate and xylohydrolysate, which are established prebiotics. Konjac flour, pectin and xylan were hydrolysed using the appropriate concentration of cellulase, pectinase and xylanase respectively. The hydrolysates produced were added to the MRS agar substituting the glucose in the original recipe. A serial dilution with the maximum recovery diluents was made and lactic acid bacteria were subcultured and incubated under 5% $CO_2$ conditions at 37° C. for 40 hours.

TABLE 3

Colony forming units and colony size (mm) of Lactobacillus and Bifidobacteria grown on MRS agar, MRS with konjac hydrolysate (KOS), MRS with pectic hydrolysate (POS) and MRS with xylohydrolysate (XOS).

| Probiotic strain | MRS | MRS + KOS | MRS + POS | MRS + XOS |
| --- | --- | --- | --- | --- |
| L. casei NCFB 161 | $4.7 \times 10^7$ (2.5 mm) | $3.2 \times 10^7$ (3.5 mm) | $4.8 \times 10^7$ (2.0 mm) | $3.7 \times 10^7$ (1.0 mm) |
| L. delbruckii NCFB 1489 | $1.3 \times 10^7$ (2.0 mm) | $1.0 \times 10^7$ (3.5 mm) | $1.1 \times 10^7$ (1.5 mm) | $1.1 \times 10^7$ (1.0 mm) |
| L. acidophilus NCFB 1748 | $2.2 \times 10^7$ (2.0 mm) | $1.8 \times 10^7$ (4.0 mm) | $1.6 \times 107$ (1.5 mm) | $1.9 \times 107$ (1.0 mm) |
| B. adolescentis NCIMB 702204 | $3.3 \times 10^7$ (2.5 mm) | $3.1 \times 10^7$ (3.5 mm) | $3.3 \times 10^7$ (2.5 mm) | $4.2 \times 10^7$ (1.0 mm) |
| B. breve NCIMB 702258 | $8.1 \times 10^7$ (2.0 mm) | $1.0 \times 10^8$ (2.5 mm) | $1.3 \times 10^8$ (0.5 mm) | $6.5 \times 10^7$ (1.0 mm) |
| B. bifidum NCIMB 700795 | $3.4 \times 10^7$ (1.5 mm) | $3.5 \times 10^7$ (1.5 mm) | $2.1 \times 10^7$ (0.25 mm) | $3.4 \times 10^7$ (0.25 mm) |

The results as shown in Table 3 of C.F.U. with all carbon sources were similar with the exception of B. breve NCIMB (702258) which showed higher counts ($1.0 \times 10^8$) where konjac and pectic hydrolysates were available. However, the size of colonies on media containing konjac hydrolysate was bigger than those grown on MRS agar, pectic hydrolysate and xylohydrolysate, shown in FIG. 5.

EXAMPLE 5

Use of Glucomannan/Konjac Hydrolysate in Non-Fermented/to be Fermented/Fermented Foods Konjac Hydrolysate and Inulin in UHT Milk:

A comparison was conducted on the growth of lactic acid bacteria on konjac hydrolysate and inulin as a commercial hydrolysate. UHT milk was purchased and examined in terms of growth of lactic acid bacteria by using the incorporated hydrolysate as a carbon source. Samples of milk (control), milk with 2% konjac hydrolysate and milk with 2% inulin were incubated under 5% $CO_2$ conditions at 37° C. for 24 hours. A serial dilution with maximum recovery diluents was made and 0.1 ml aliquot of each dilution of each organism was plated using spread plate technique. Plates were then incubated under 5% $CO_2$ conditions at 37° C. for 48 hours, after which time colony forming units (C.F.U.) were obtained.

TABLE 4

Difference in colony forming units (C.F.U.)/ml of milk, milk with inulin and milk with konjac hydrolysate (KOS) subcultured on MRS agar.

| Probiotic strain | milk | milk + inulin | milk + KOS |
|---|---|---|---|
| L. casei NCFB 161 | $6.5 \times 10^7$ | $6.7 \times 10^7$ | $4.3 \times 10^8$ |
| L. delbruckii NCFB 1489 | $4.0 \times 10^7$ | $7.4 \times 10^7$ | $4.9 \times 10^8$ |
| L. acidophilus NCFB 1748 | $3.2 \times 10^7$ | $3.7 \times 10^7$ | $7.4 \times 10^8$ |
| B. adolescentis NCIMB 702204 | $4.6 \times 10^7$ | $5.3 \times 10^7$ | $6.6 \times 10^8$ |
| B. breve NCIMB 702258 | $4.1 \times 10^8$ | $7.6 \times 10^8$ | $1.5 \times 10^9$ |
| B. bifidum NCIMB 700795 | $1.3 \times 10^8$ | $2.0 \times 10^8$ | $1.6 \times 10^9$ |

The results shown in Table 4 and FIG. 6 show that colony forming units in milk containing konjac hydrolysate were higher ($4.3 \times 10^8$ to $1.6 \times 10^9$) than those in milk with inulin ($3.7 \times 10^7$ to $7.6 \times 10^8$), and this in turn was very similar to the milk only. In addition, colony forming units of bifidobacteria were higher than lactobacilli in all samples.

Konjac Hydrolysate and Natural Yoghurt:

The effect of konjac hydrolysate on the growth of lactic acid bacteria was tested further by applying this product to the natural yoghurt. The flora of the natural yoghurt was determined immediately, and 0, 1, 2 and 5% of konjac hydrolysate were added into the yoghurt which was incubated at 37° C. for 48 hours. A serial dilution with maximum recovery diluents was made and 0.1 ml aliquot of each dilution was plated using spread plate technique. Plates were then incubated under 5% $CO_2$ conditions at 37° C. for 48 hours, after which time colony forming units (C.F.U.) were obtained.

TABLE 5

Colony forming units (C.F.U.)/g yoghurt containing different concentrations of konjac hydrolysate.

| konjac hydrolysate added, % | Dilution selected | Average no. of colonies | Colony forming units (C.F.U.) per gram Yoghurt |
|---|---|---|---|
| 0 | $10^{-4}$ | 128 | $1.3 \times 10^7$ |
| 1 | $10^{-4}$ | 181 | $1.8 \times 10^7$ |
| 2 | $10^{-4}$ | 204 | $2.0 \times 10^7$ |
| 5 | $10^{-4}$ | 108 | $1.1 \times 10^7$ |

The results shown in Table 5 showed a very slight increase in the number of colonies as the concentration of the konjac hydrolysate increased ($1.3 \times 10^7$, $1.8 \times 10^7$ and $2.0 \times 10^7$) with the exception of 5% increase of hydrolysate which formed so much acid that growth was restricted.

EXAMPLE 6

Potential of Glucomannan/Konjac Hydrolysate to Promote Growth in Feeds/Foods and within the Gut and Body An investigation was carried out to examine the potential effect of glucomannan/konjac hydrolysate to promote growth in feed/foods and exert a beneficial influence on human health by inhibiting the growth of other microorganisms including pathogenic bacteria in the gut. As it is well known that chicken usually spoiled with pathogenic bacteria such as Campylobacter and Listeria, therefore, 25 g of chicken breast was homogenised using a stomacher and used to inoculate 200 ul into 20 ml Mueller Hinton broth (oxoid) in 50 ml conical flask. This was incubated for overnight at 37° C. on an orbital shaker. On the same day as this was constructed, a growth spot was created by inoculating loopful of overnight incubated cultures of the probiotic bacteria (L. casei, L. acidophilus and B. adolescentis) on the centre of MRS agar with konjac hydrolysate as a carbon source substituting the glucose in the original recipe (20 mg/ml glucose). Plates were incubated overnight under 5% $CO_2$ conditions at 37° C. A quantity of 200 ul of the overnight incubated Mueller Hinton broth containing the chicken mixture was added into 15 ml of MH agar for each organism. The added culture was gently mixed with the molten agar and then poured into petri dishes and allowed to solidify. The agar was then aseptically removed from the plates by gently lifting it and slowly lowering it on the spot of the probiotic growth on the other agar plates. The plates with the sandwiched agar were incubated in aerobic conditions at 37° C. Following overnight incubation, the zone of inhibition where no bacterial growth over the probiotic spot was measured and the diameter of the probiotic spot for each strain was subtracted from this figure. This experimental work was repeated three times and consistently produced results.

The above procedures were also applied to two pure cultures of pathogenic Listeria monocytogenes, one culture of Escherichia coli and one culture of Staphylococcus aureus. Listeria monocytogenes L850, from milk and Listeria monocytogenes Scott A, from human source were initially subcultured in TSB, then their inhibition with the probiotic bacteria L. acidophilus NCFB 1748; L. plantarum DSM 12028; L. casei ssp casei NCFB 161 and Lactococcus lactis ssp lactis NCIMB 6681 (Hannah Research Institute, Ayr, Scotland) was investigated.

E. coli was grown in Luria broth before its inhibition was tested against the probiotic bacteria L. casei ssp casei NCFB 161 and *L. acidophilus* NCFB 1748 on MRS and MRS supplemented with glucomannan. *Staphylococcus aureus* was grown in Mueller Hinton broth prior to investigating its inhibition by *L. acidophilus* NCFB 1748, *L. casei* ssp *casei* NCFB 161, *L. gasseri* NCFB 2233 and *Lactococcus lactis* ssp *lactis* NCIMB 6681.

As this invented prebiotic has unique profiles that make it universally valuable in a wide range of technologies including food, feed and healthcare/pharmaceutical applications, it would be very beneficial to apply this prebiotic as a biotherapeutic agent, in particular, for the control and treatment of candidiasis and vaginosis. Therefore preliminary investigations were conducted using the yeast *Candida albicans*.

A growth spot was created by inoculating loopful of overnight incubated cultures of the prebiotic bacteria (*L. acidophilus* NCFB 1748, *L. casei* NCFB 161, *L. gasseri* NCFB 2233, *L. planarum* DSM 12028 and *Lactococcus lactis* NCIMB 6681) on the centre of MRS agar and MRS agar supplemented with konjac hydrolysate. Plates were incubated overnight under 5% $CO_2$ conditions at 37° C. A quantity of 10 ml of Sabouraud dextrose agar, Oxoid (soft agar 0.7%) maintained at 50° C. was inoculated with 100 ul *Candida albicans* grown overnight at 30° C. The added amount was mixed well with the molten agar, and then overlaid on the solidified agar containing the probiotic spot. The plates were incubated in aerobic conditions at 30° C. for the yeast to grow. Following overnight incubation, the zone of inhibition where no yeast growth over the prebiotic spot was measured and the diameter of the prebiotic spot for each strain were subtracted from this figure.

It was shown that lactic acid bacteria produced an inhibition zone to the mixed culture from the chicken extract when inoculated on MRS agar or modified MRS agar containing konjac hydrolysate. This was well demonstrated on modified MRS agar in particular with the strain *Lactobacillus acidophilus* which showed an inhibition zone of 18 mm. The other two strains ((*L. casei* and *B. adolescentis*) showed an inhibition zone of 15 mm. However, strains inoculated on MRS agar showed only 11 mm inhibition zone.

TABLE 6

Inhibition zone of Listeria monocytogenes, Escherichia coli, Staphylococcus aureus and Candida albicans by Lactic acid bacteria on MRS media. KOS = konjac hydrolysate

| Strain | MRS agar | MRS + KOS (+glucose) | MRS + KOS (−glucose) |
|---|---|---|---|
| *Listeria monocytogenes* L850 | | | |
| *L. acidophilus* NCFB 1748 | 11 | 19 | 10 |
| *L. plantarum* DSM 12028 | 11 | 24 | 12 |
| *L. casei* ssp *casei* NCFB 161 | 14 | — | 9 |
| *Lactococcus lactis* ssp *lactis* NCIMB6681 | 12 | 21 | 5 |
| *Listeria monocytogenes* Scott A | 13 | 19 | 10 |
| *L. acidophilus* NCFB 1748 | 14 | 24 | 12 |
| *L. plantarum* DSM 12028 | 14 | — | 14 |
| *L. casei* ssp *casei* NCFB 161 | 13 | 21 | 5 |
| *Lactococcus lactis* ssp *lactis* NCIMB 6681 | | | |
| *Escherichia coli* | | | |
| *L. acidophilus* NCFB 1748 | 13 | — | 12 |
| *L. casei* ssp *casei* NCFB 161 | 15 | — | 14 |
| *Staphylococcus aureus* | | | |
| *L. acidophilus* NCFB 1748 | 21 | — | 16 |
| *L. casei* ssp *casei* NCFB 161 | 21 | — | 8 |
| *Lactococcus lactis* ssp *lactis* NCIMB 6681 | 22 | | 4 |
| *L. gasseri* NCFB 2233 | 20 | | 1 |
| *Candida albicans* | | | |
| *L. acidophilus* NCFB 1748 | 3 | — | 6 |
| *L. casei* ssp *casei* NCFB 161 | 4 | — | 7 |
| *Lactococcus lactis* ssp *lactis* NCIMB 6681 | 5 | | 8 |
| *L. gasseri* NCFB 2233 | 2 | — | 3 |
| *L. plantarum* | 0 | — | 0 |

The results (Table 6) also showed that *Listeria monocytogenes*, *E. coli*, *Staphylococcus aureus* and *Candida albicans* were inhibited with the lactic acid bacteria in the presence of glucomannan hydrolysate in the form of an inhibition zone (FIGS. 9, 19, 11 and 12 respectively). It seems that this inhibition was probiotic strain and carbon source dependent. The inhibition shown by lactic acid bacteria to pathogens in the presence of glucomannan (prebiotic) is very important. In particular, to *Candida albicans* as it is a significant approach towards finding a therapy for vaginal episodes and re-establishing a healthy vaginal microflora. This approach enables the inventors to expand the definition of biotherapeutic agent and its use even further, by introducing administrative prebiotic or/and probiotic in any form such as pessaries, creams or gels for the control and treatment of vaginal infections.

The work carried out by the Applicant shows that glucomannan hydrolysates, and in particular, konjac glucomannan hydrolysates act as a superior probiotic substance and have an unexpectedly greater efficacy in promoting bacterial cell growth. In general, it was found that cells had a shorter generation time and multiplied much more rapidly in the presence of glucomannan hydrolysates than with other established probiotic substances.

Further modifications and alterations may be made within the scope of the invention herein described.

REFERENCES

Behr, W. (1998) Dietetic and pharmaceutical raw material. www.behrbonn.com/literat/konjacmb.htm Brandt, L. A. (2001) Prebiotics enhance gut health. www.findarticles.com/cf_dls/m3289/9__170/78576180/print.jhtml Burrington, K. J. (1999) Inside cookies and crackers. www.foodproductdesign.com/archive/1999/0799de.html Cescutti, P., Campa, C., Delben, F. and Rizzo, R. (2002) *Carbohydrate Research* 337, 2505-2511.

Chiu, C-W, Jeffcoat, R., Zallie, J. P. and Henley, M. (1991) EP0457098.

Chiu, C-W, Jeffcoat, R., Zallie, J. P. and Henley, M. (1998) U.S. Pat. No. 5,811,148.

Chiu, C-W, Jeffcoat, R., Zallie, J. P. and Henley, M. (2002) US2002051841.

Edashige, Y. and Ishii, T. (1998) *Phytochemistry* 49, 1675-1682.

Jones, P. J. (2002) Clinical nutrition: 7. Functional foods—more than just nutrition. *Canadian Medical Association Journal* 166 (12), 1555-1563.

Kato, K. and Matsuda, K. (1969) *Agricultural and Biological Chemistry* 33, 1446-1453.

Kato, K., Watanabe, T. and Matsuda, K. (1970) *Agricultural and Biological Chemistry* 34, 532-539.

Khanna, S. (2003) The Chemical, Physical and Nutritional Properties of the Plant Polysaccharide Konjac Glucomannan. PhD Thesis, Glasgow Calcdonian University, Glasgow, UK.

King, L. V., Erkoboni, F. D. and Wheatley, O. T. (1994) WO9415643.

Kurakake, M. and Komaki, T. (2001) *Current Microbiology* 42, 377-380.

Ohya, Y., Ihara, K., Murata, J., Sugitou, T. and Ouchi, T. (1994) *Carbohydrate Polymers* 25, 123-130.

Loo, J. V., Cummings, J., Delzenne, N., Englyst, H., Franck, A., Hopkins, M., Kok, N., Macfarlane, G., Newton, D., Quigley, M., Roberfroid, M., van Vliet, T. and van den Heuvel, E. (1999) *British Journal of Nutrition* 81, 121-132.

Nelson, N. (1944) Journal of Biological Chemistry 153, 375.

Platzman, A. (2000) www.foodproductdesign.com/archive/2000/0100nn.html

Qi, L., Li, G. J. and Zong, M. H. (2003) *ACTA Polymerica Sinica* 5, 650-654.

Shimahara, H., Suzuki, H., Sugiyama, N. and Nizakawa, K. (1975) *Agricultural and Biological Chemistry* 39, 293-299.

Sugiyama, N. and Shimahara, H. (1976) U.S. Pat. No. 3,973,008. Shimizu Manzo Shoten KK (1974) GB1351006. Sun, G. (2003) US2003138545.

Thomas, W. R. (1997) In Thickening and Gelling Agents for Foods (A. Imeson, Ed), pp 169-179. Blackie: London.

Tomasik, P. J. and Tomasik, P. (2003) *Cereal Chemistry* 80, 113-117.

Topping, D. L. and Clifton, P. M. (2001) *Physiological Reviews* 81, 1031-1064.

Tye, J. R., Bullens, C. W. and Llanto, M. G. (1990) WO9015544.

Tye, J. R., Bullens, C. W. and Llanto, M. G. (1994) U.S. Pat. No. 5,308,636.

Vuksan, V. (2001) CA2410556.

Wheatley, O. T., King, L. V. and Erkoboni, F. D. (1996) U.S. Pat. No. 5,486,364.

Zhou, W. (1995) CN1097114.

The invention claimed is:

1. A prebiotic for promoting the growth of microorganisms in man and animals, the prebiotic comprising a konjac glucomannan cellulase hydrolysate, wherein the prebiotic is in the form of a pessary, cream or suppository.

2. A synbiotic food or feed comprising one or more probiotic bacteria and a cellulase hydrolysate of a konjac glucomannan.

3. A synbiotic food or feed as claimed in claim 2, wherein the probiotic bacteria is Lactic acid bacteria.

4. A pharmaceutical composition comprising one or more probiotic bacteria and a cellulase hydrolysate of a konjac glucomannan.

5. A pharmaceutical composition as claimed in claim 4, in the form of a pessary.

6. A pharmaceutical composition as claimed in claim 4, in the form of a suppository.

7. A pharmaceutical composition as claimed in claim 4, in the form of a cream.

8. A method of manufacturing a prebiotic, for promoting the growth of microorganisms in man and animals, the method comprising the steps of:
   a) dissolving a konjac glucomannan containing flour in an aqueous solution;
   b) adding a cellulase to the aqueous solution to form konjac glucomannan cellulase hydrolysate fractions; and
   c) extracting the konjac glucomannan cellulase hydrolysate fractions from the aqueous solution;
   wherein said konjac glucomannan cellulase hydrolysate fractions can be used as a prebiotic.

9. A method for promoting growth of microbial cells in a subject comprising administering a konjac glucomannan cellulase hydrolysate to a subject, wherein administering the konjac glucomannan cellulase hydrolysate promotes the growth of microbial cells.

10. The method of claim 9, wherein the konjac glucomannan is a flour.

11. The method of claim 9, wherein the microbial cells are bacteria.

12. The method of claim 11, wherein the bacteria are Lactic acid bacteria.

13. The method of claim 9, wherein the konjac glucomannan cellulase hydrolysate is administered within an animal or human foodstuff.

14. The method of claim 13, wherein the foodstuff is a functional food.

15. The method of claim 13, wherein the foodstuff is a fermenting or fermented product.

16. The method of claim 13, wherein the foodstuff promotes growth of microbial cells within the intestine and body cavities.

17. The method of claim 13, wherein the foodstuff promotes growth of gut friendly microbial cells at the expense of a pathogenic organism.

18. The method of claim 9, wherein the microbial cell growth is promoted in the gut of humans and animals.

19. The method of claim 9, wherein the microbial cell growth is promoted in the body cavities of humans and animals.

20. The method of claim 19, wherein the microbial cell growth is promoted in the vagina.

21. The method of claim 9, wherein the microbial cell growth is promoted on the skin of humans and animals.

22. The method of claim 17, wherein the pathogenic organism is selected from the group consisting of: *Listeria monocytogenes*; *Escherichia coli*; and *Staphyloccus aureus*.

23. A method for the treatment of candidiasis in a subject, comprising administering an effective amount of the konjac glucomannan cellulase hydrolysate to the subject, wherein the effective amount is sufficient to inhibit growth of *Candida albicans*.

* * * * *